US012588611B2

(12) United States Patent
Gray

(10) Patent No.: US 12,588,611 B2
(45) Date of Patent: Mar. 31, 2026

(54) FERTILIZER MANAGEMENT

(71) Applicant: BASF PLANT SCIENCE COMPANY GMBH, Ludwigshafen (DE)

(72) Inventor: Kristin Gray, Fort Collins, CO (US)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 0 days.

(21) Appl. No.: 18/282,888

(22) PCT Filed: Mar. 25, 2022

(86) PCT No.: PCT/US2022/021846
§ 371 (c)(1),
(2) Date: Sep. 19, 2023

(87) PCT Pub. No.: WO2022/204454
PCT Pub. Date: Sep. 29, 2022

(65) Prior Publication Data
US 2024/0164269 A1      May 23, 2024

Related U.S. Application Data

(60) Provisional application No. 63/166,110, filed on Mar. 25, 2021.

(51) Int. Cl.
*A01H 3/04*      (2006.01)
*A01H 6/20*      (2018.01)

(52) U.S. Cl.
CPC .............. *A01H 3/04* (2013.01); *A01H 6/202* (2018.05)

(58) Field of Classification Search
None
See application file for complete search history.

(56) References Cited

U.S. PATENT DOCUMENTS

| | | | | |
|---|---|---|---|---|
| 6,303,849 | B1 | 10/2001 | Potts et al. | |
| 7,423,198 | B2 | 9/2008 | Yao et al. | |
| 7,807,849 | B2 | 10/2010 | Singh et al. | |
| 2018/0298400 | A1* | 10/2018 | Senger | C12N 15/8247 |
| 2019/0256862 | A1* | 8/2019 | Andre | C12N 15/8247 |

FOREIGN PATENT DOCUMENTS

| | | | |
|---|---|---|---|
| WO | WO-01/59128 | A2 | 8/2001 |
| WO | WO-02/26946 | A2 | 4/2002 |
| WO | WO-03/078639 | A2 | 9/2003 |
| WO | WO-03/093482 | A2 | 11/2003 |
| WO | WO-2004/071467 | A2 | 8/2004 |
| WO | WO-2004/087902 | A2 | 10/2004 |
| WO | WO-2004/090123 | A2 | 10/2004 |
| WO | WO-2005/007845 | A2 | 1/2005 |
| WO | WO-2005/012316 | A2 | 2/2005 |
| WO | WO-2005/083053 | A2 | 9/2005 |
| WO | WO-2005/083093 | A2 | 9/2005 |
| WO | WO-2006/008099 | A2 | 1/2006 |
| WO | WO-2006/069710 | A1 | 7/2006 |
| WO | WO-2006/100241 | A2 | 9/2006 |
| WO | WO-2007/096387 | A1 | 8/2007 |
| WO | WO-2008/022963 | A2 | 2/2008 |
| WO | WO-2010/066703 | A2 | 6/2010 |
| WO | WO-2013/153404 | A1 | 10/2013 |
| WO | WO-2015/089587 | A1 | 6/2015 |
| WO | WO-2016/075303 | A1 | 5/2016 |
| WO | WO-2016/075325 | A1 | 5/2016 |
| WO | WO-2016/075327 | A2 | 5/2016 |
| WO | WO-2017/210426 | A1 | 12/2017 |
| WO | WO-2017/219006 | A1 | 12/2017 |

OTHER PUBLICATIONS

"Nitrogen." Canola Encyclopedia, edited by Canola Council of Canada, https://www.canolacouncil.org/canola-encyclopedia/fertility/nitrogen/; Accessed Feb. 7, 2025 (Year: 2025).*
Li, Siting, et al. "Effect of nitrogen sources on Omega-3 polyunsaturated fatty acid biosynthesis and gene expression in *Thraustochytriidae* sp." Marine Drugs 18.12 (2020): 612. (Year: 2020).*
Hao, Pengfei, et al. "Transcriptomic analysis of the reduction in seed oil content through increased nitrogen application rate in rapeseed (*Brassica napus* L.)." International Journal of Molecular Sciences 24.22 (2023): 16220. (Year: 2023).*
Gao, Juan, et al. "Effects of manure and fertilizer applications on canola oil content and fatty acid composition." Agronomy Journal 102.2 (2010): 790-797. (Year: 2010).*
Beyzi et al., Changes in fatty acid and mineral composition of rapeseed (*Brassica napus* ssp. *oleifera* L.) oil with seed sizes, Industrial Crops and Products, 129:10-14 (2019).
Pan et al., The effect of cultivar, seeding rate and applied nitrogen on *Brassica carinata* seed yield and quality in contrasting environments, Canadian Journal of Plant Science, 92(5):961-71 (2012).
International Application No. PCT/US2022/021846, International Search Report and Written Opinion, mailed Jul. 15, 2022.

* cited by examiner

*Primary Examiner* — Weihua Fan
(74) *Attorney, Agent, or Firm* — MARSHALL, GERSTEIN & BORUN LLP

(57) ABSTRACT

Provided herein are various aspects related to increasing the proportion of omega-3 fatty acid in seed oil produced by a plurality of *Brassica* plants, which have been modified to produce seed oil comprising at least one of EPA, DHA and DPA. It relates to a method to increase the proportion of long-chain omega-3 fatty acid in seed oil produced by a plurality of *Brassica* oilseed plants comprising growing the *Brassica* oilseed plants in the presence of an increased amount of nitrogen as compared to a standard amount of nitrogen, wherein the *Brassica* oilseed plants have been modified to produce seed oil with at least one of EPA, DHA and DPA.

22 Claims, No Drawings

FERTILIZER MANAGEMENT

CROSS-REFERENCE TO RELATED APPLICATIONS

This is the U.S. national phase of International Application No. PCT/US2022/021846, filed Mar. 25, 2022, which claims the benefit of U.S. Provisional Patent Application No. 63/166,110, filed Mar. 25, 2021, incorporated herein by reference in its entirety.

BACKGROUND OF THE INVENTION

Omega-3 fatty acids are polyunsaturated fatty acids which convey a range of health benefits and aid in healthy development in humans and other animals. Farmed fish provide humans with a dietary source of omega-3 fatty acids, but fish also need omega-3 fatty acids, particularly long-chain omega-3 fatty acids which would typically be obtained from marine sources in the wild. Aquaculture currently consumes what amounts to a majority of the global supply of omega-3 fatty acids. Historically, farmed fish were provided feed obtained from marine sources to deliver nutrients. However, providing farmed fish with nutrients sourced from wild marine sources may exacerbate declining wild fish populations and stress other ocean resources. Although certain omega-3 fatty acids are readily available from plant sources, plant-based diets typically fail to provide sufficient dietary amounts of the type of long chain omega-3 fatty acids found in marine oils. Long chain omega-3 fatty acids include EPA (eicosapentaenoic acid), DPA (docosapentaenoic acid) and DHA (docosahexaenoic acid). Other sources of long chain omega-3 fatty acids include microalgae or production via bioreactors.

Recently, new terrestrial, plant-based sources of long chain omega-3 fatty acids have been described. For example, oilseed plants, such as canola and other *Brassica* plants, have been genetically modified to provide long chain omega-3 fatty acids including EPA, DPA and DHA (WO 2016/075303, WO 2016/075325, WO 2016/075327, WO 2015/089587, WO2013/153404, WO 2004/071467 and U.S. Pat. No. 7,807,849 B2). Such plant-sourced omega-3 fatty acids can be used alone or together with marine-sourced omega-3 fatty acids to supplement or wholly provide a dietary source of omega-3 fatty acids, including long chain omega-3 fatty acids (WO 2017/210426). Transgenic canola can be a scalable, plant-based source of long chain omega-3 fatty acids. Such plants have the advantage of providing a source of long chain omega-3 fatty acid that does not disrupt or deplete natural marine resources.

Canola is an example of a *Brassica* plant crop that is an affordable and healthy source of dietary oil. Canola plants are grown globally and harvested for their seeds which have a high oil content. For example, canola seeds can contain 44% oil, which is double the oil content of soybeans.

SUMMARY OF THE INVENTION

The present invention provides a *Brassica* fertilizer management method for improving crop yields, such as oil yields from *Brassica* plants seeds, such as long chain omega 3 fatty acids, including an increase in omega-3 docosahexaenoic acid (DHA), docosapentaenoic acid (DPA), and/or eicosapentaenoic acid (EPA) as compared to plants not grown according to the methods described herein.

One aspect provides a method to increase the proportion of long-chain omega-3 fatty acid in seed oil produced by a plurality of *Brassica* oilseed plants comprising growing the *Brassica* oilseed plants in the presence of an increased amount of nitrogen as compared to a standard amount of nitrogen, wherein the *Brassica* oilseed plants have been modified to produce seed oil with at least one of EPA, DHA and DPA.

In one aspect, the increased amount of nitrogen is 30-50% increase over a standard amount nitrogen. In one aspect, the increased amount of nitrogen is 30%, 31%, 32%, 33%, 34%, 35%, 36%, 37%, 38%, 39%, 40%, 41%, 42%, 43%, 44%, 45%, 46%, 47%, 48%, 49% or 50% increase over a standard amount nitrogen. In another aspect, the increased amount of nitrogen is 30 lbs/acre to 90 lbs/acre, including 30 lbs/acre to 70 lbs/acre, 70 lbs/acre to 90 lbs/acre, 50 lbs/acre or 70 lbs/acre increase over a standard amount nitrogen. In one aspect, the increased amount nitrogen is 30 lbs/acre, 31 lbs/acre, 32 lbs/acre, 33 lbs/acre, 34 lbs/acre, 35 lbs/acre, 35 lbs/acre, 36 lbs/acre, 37 lbs/acre, 38 lbs/acre, 39 lbs/acre, 40 lbs/acre, 41 lbs/acre, 42 lbs/acre, 43 lbs/acre, 44 lbs/acre, 45 lbs/acre, 46 lbs/acre, 47 lbs/acre, 48 lbs/acre, 49 lbs/acre, 50 lbs/acre, 51 lbs/acre, 52 lbs/acre, 53 lbs/acre, 54 lbs/acre, 55 lbs/acre, 56 lbs/acre, 57 lbs/acre, 58 lbs/acre, 59 lbs/acre, 60 lbs/acre, 61 lbs/acre, 62 lbs/acre, 63 lbs/acre, 64 lbs/acre, 65 lbs/acre, 66 lbs/acre, 67 lbs/acre, 68 lbs/acre, 69 lbs/acre, 70 lbs/acre, 71 lbs/acre, 72 lbs/acre, 73 lbs/acre, 74 lbs/acre, 75 lbs/acre, 76 lbs/acre, 77 lbs/acre, 78 lbs/acre, 79 lbs/acre, 80 lbs/acre, 81 lbs/acre, 82 lbs/acre, 83 lbs/acre, 84 lbs/acre, 85 lbs/acre, 86 lbs/acre, 87 lbs/acre, 88 lbs/acre, 89 lbs/acre or 90 lbs/acre nitrogen over a standard amount of nitrogen.

In another aspect, the standard amount of nitrogen is 100 lbs/acre to 200 lbs/acre, including 100 lbs/acre to 150 lbs/acre, 125 lbs/acre, 150 lbs/acre to 200 lbs/acre or 175 lbs/acre. In one aspect, the standard amount of nitrogen is 100 lbs/acre, 101 lbs/acre, 102 lbs/acre, 103 lbs/acre, 104 lbs/acre, 105 lbs/acre, 106 lbs/acre, 107 lbs/acre, 108 lbs/acre, 109 lbs/acre, 110 lbs/acre, 111 lbs/acre, 112 lbs/acre, 113 lbs/acre, 114 lbs/acre, 115 lbs/acre, 11 lbs/acre, 117 lbs/acre, 118 lbs/acre, 119 lbs/acre, 120 lbs/acre, 121 lbs/acre, 122 lbs/acre, 12 lbs/acre, 124 lbs/acre, 125 lbs/acre, 126 lbs/acre, 127 lbs/acre, 128 lbs/acre, 129 lbs/acre, 130 lbs/acre, 131 lbs/acre, 132 lbs/acre, 133 lbs/acre, 134 lbs/acre, 135 lbs/acre, 136 lbs/acre, 137 lbs/acre, 138 lbs/acre, 139 lbs/acre, 140 lbs/acre, 141 lbs/acre, 142 lbs/acre, 143 lbs/acre, 144 lbs/acre, 145 lbs/acre, 146 lbs/acre, 147 lbs/acre, 148 lbs/acre, 149 lbs/acre, 150 lbs/acre, 151 lbs/acre, 152 lbs/acre, 153 lbs/acre, 154 lbs/acre, 155 lbs/acre, 156 lbs/acre, 157 lbs/acre, 158 lbs/acre, 159 lbs/acre, 160 lbs/acre, 161 lbs/acre, 162 lbs/acre, 163 lbs/acre, 164 lbs/acre, 165 lbs/acre, 166 lbs/acre, 167 lbs/acre, 168 lbs/acre, 169 lbs/acre, 170 lbs/acre, 171 lbs/acre, 172 lbs/acre, 173 lbs/acre, 174 lbs/acre, 175 lbs/acre, 176 lbs/acre, 177 lbs/acre, 178 lbs/acre, 179 lbs/acre, 180 lbs/acre, 181 lbs/acre, 182 lbs/acre, 183 lbs/acre, 184 lbs/acre, 185 lbs/acre, 186 lbs/acre, 187 lbs/acre, 188 lbs/acre, 189 lbs/acre, 190 lbs/acre, 191 lbs/acre, 192 lbs/acre, 193 lbs/acre, 194 lbs/acre, 195 lbs/acre, 196 lbs/acre, 197 lbs/acre, 19 lbs/acre, 19 lbs/acre or 200 lbs/acre.

In one aspect, the nitrogen is applied dry, wet or a combination thereof. In one aspect, *Brassica* oilseed plants are planted in a field. In one aspect, the fields are irrigated. In another aspect, the fields are not irrigated.

In one aspect, the *Brassica* oilseed plants are *Brassica napus* plants.

In another aspect, the of omega-3 fatty acid in the seed oil is increased in the presence of an increased amount of nitrogen during growth in comparison to control *Brassica* oilseed plants grown in the presence of a standard amount of nitrogen. In aspect, the percent increase in combined EPA, DPA and DHA when grown in the presence of an increased amount of nitrogen is 3.9-7%. In another aspect, the percent increase in EPA when grown in the presence of an increased amount of nitrogen is 3-6%. In one aspect, the percent increase in DPA when grown in the presence of an increased amount of nitrogen is 3-7%. In another aspect, the percent increase in DHA when grown in the presence of an increased amount of nitrogen is 7-20%.

In aspect, the *Brassica* plants are harvested when 80% to 100% color change has occurred on the first raceme of the plants. In another aspect, a color change has further occurred on 80% to 100% of the second, third and/or fourth raceme of the plants prior harvesting. In another aspect, the color change has occurred on 80% to 100% of the third raceme of the plants prior to harvesting.

One aspect provides *Brassica* plant seeds comprising seed oil which comprises at least 9.5-11 wt % long chain omega-3 fatty acids. In one aspect, the seed oil comprises at least 7-8.8 wt % EPA. In another aspect, the seed oil comprises at least 1-2.5 wt % DPA. In one aspect, the seed oil comprises at least 0.55-0.9 wt % DHA.

One aspect provides *Brassica* plant seeds comprising seed oil which is at least 9.5-11 wt % long chain omega-3 fatty acids made by the methods as provided herein In one aspect, the seed oil comprises at least 7-8.8 wt % EPA. In another aspect, the seed oil comprises at least 1-2.5 wt % DPA. In one aspect, the seed oil comprises at least 0.55-0.9 wt % DHA.

DETAILED DESCRIPTION OF THE INVENTION

A goal of growing/farming *Brassica* plants is to produce a larger yield of seeds, oil from seeds and/or seeds with a particular or desired oil composition/oil profile. Provided herein are methods to increase oil production in *Brassica* plants and/or obtain a desired oil profile/composition (including but not limited to long chain omega-3 fatty acids) based on fertilizer.

The present disclosure provides a method of increasing the proportion of long-chain omega-3 fatty acid in seed oil produced by a plurality of transgenic *Brassica* oilseed plants, comprising subjecting the transgenic *Brassica* oilseed plants to specific fertilizer amounts; and wherein the transgenic *Brassica* oilseed plants have been transgenically modified to produce seed oil comprising at least one of EPA, DHA and DPA. This method can also be combined with a method of increasing the proportion of long-chain omega-3 fatty acid in seed oil produced by a plurality of transgenic *Brassica* oilseed plants, comprising subjecting the transgenic *Brassica* oilseed plants to specific harvesting times; and wherein the transgenic *Brassica* oilseed plants have been transgenically modified to produce seed oil comprising at least one of EPA, DHA and DPA.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Definitions of particular terms may be contained within this section or may be incorporated into the sections of text below.

When a particular feature, structure, or characteristic is described in connection with an aspect, it is submitted that it is within the knowledge of one skilled in the art to affect such feature, structure, or characteristic in connection with other aspects whether or not explicitly described.

As used herein, the articles "a" and "an" refer to one or to more than one, i.e., to at least one, of the grammatical object of the article. By way of example, "an element" means one element or more than one element.

Values expressed in a range format should be interpreted in a flexible manner to include not only the numerical values explicitly recited as the limits of the range but also to include all the individual numerical values or sub-ranges encompassed within that range as if each numerical value and sub-range is explicitly recited. For example, a concentration range of "0.1% to 5%" should be interpreted to include not only the explicitly recited concentration of 0.1 wt. % to 5 wt. %, but also the individual concentrations (e.g., 1%, 2%, 3%, and 4%) and the sub-ranges (e.g., 0.1% to 0.5%, 1.1% to 2.2%, and 3.3% to 4.4%) within the indicated range.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "substantially" as used herein refers to a majority of, or mostly, as in at least 50%, 60%, 70%, 80%, 90%, 95%, 96%, 97%, 98%, 99%, 99.5%, 99.9%, 99.99%, or at least 99.999% or more, or 100%.

The term "oil" as used herein can refer to a substance formed primarily of fatty acids. An oil herein may be either liquid or solid at room temperature and may be in liquid or solid form (e.g. a dry fat). Oils can refer be formed primarily of fatty acids, for instance in triglyceride or phospholipid (e.g. lecithin) form. Examples of oils herein include various vegetal oils such as *Brassica* oils as well as marine oils such as fish oil or krill oil, animal fats such as poultry fat, and phospholipids such as soy lecithin. Oils may also include other compounds often associated with fats such as sterols, e.g. cholesterol, or tocopherols.

The term "fatty acid" as used herein can refer to a molecule comprising a hydrocarbon chain and a terminal carboxylic acid group. As used herein, the carboxylic acid group of the fatty acid may be modified or esterified, for example as occurs when the fatty acid is incorporated into a glyceride or a phospholipid or is attached to another molecule such as acetyl-CoA (e.g., COOR, where R refers to, for example, a carbon atom). Alternatively, the carboxylic acid group may be in the free fatty acid or salt form (i.e., COO or COOH).

A "saturated" fatty acid is a fatty acid that does not contain any carbon-carbon double bonds in the hydrocarbon chain. An "unsaturated" fatty acid contains one or more carbon-carbon double bonds. A "polyunsaturated" fatty acid contains more than one such carbon-carbon double bond while a "monounsaturated" fatty acid contains only one carbon-carbon double bond. Carbon-carbon double bonds may be in one of two stereo co-figurations denoted cis and trans. Naturally occurring unsaturated fatty acids are generally in the "cis" form. Unsaturated fatty acids may, for example, be of the omega-6 (or n-6 or co-6) or omega-3 (n-3 or co-3) type. Omega-6 fatty acids have a first double bond at the sixth position from the methyl end of the fatty acid chain while omega-3 fatty acids have a first double bond at the third position from the methyl end of the chain. The term "long-chain" when applied to an omega-3 or omega-6 fatty acid means having a chain of 20 carbons or more.

Fatty acids found in plants and oils described herein may be incorporated into various glycerides. The terms "triacylglycerol," "triglyceride," and "TAG" are used interchangeably herein to refer to a molecule comprising a glycerol that is esterified at each of its three hydroxyl groups by a fatty acid and thus, comprises three fatty acids. The terms "diacylglycerol," "diglyceride," and "DAG" refer to a molecule comprising a glycerol esterified by a fatty acid at only two of its three available hydroxyl groups, such that it contains only two fatty acids. Likewise, the term "monoglyceride" refers to a glycerol modified by a fatty acid at only one of the available three hydroxyl groups so that it comprises only one fatty acid.

Fatty acids found in plants and oils described herein may also be incorporated into various "phospholipids," abbreviated "PL" herein. Phospholipids are molecules that comprise a diglyceride, a phosphate group, and another molecule such as choline ("phosphatidyl choline;" abbreviated "PC" herein), ethanolamine ("phosphatidyl ethanolamine;" abbreviated "PE" herein), serine "phosphatidyl serine;" abbreviated "PS" herein), or inositol ("phosphatidyl inositol;" abbreviated "PI" herein). Phospholipids, for example, are important components of cellular membranes.

The levels of particular types of fatty acids may be provided herein in percentages out of the total fatty acid content of an oil. Unless specifically noted otherwise, such percentages are weight percentages based on the total fatty acids, TAGs, or PLs in the oil component, respectively, as calculated experimentally. Thus, for example, if a percentage of a specific species or set of fatty acids is provided, e.g., EPA or EPA+DHA or EPA+DPA+DHA, this is a w/w percentage based on the total fatty acids detected in the oil. The fatty acid composition of an oil can be determined by methods available in the art. The American Oil Chemist's Society (AOCS) maintains analytical methods for a wide variety of tests performed on vegetable oils. Hydrolysis of the oil's components to produce free fatty acids, conversion of the free fatty acids to methyl esters, and analysis by gas-liquid chromatography (GLC) is the universally accepted standard method to determine the fatty acid composition of an oil sample. The AOCS Procedure Ce 1-62 describes the procedure used.

The term "polyunsaturated fatty acids" and "PUFA" as used herein refers to fatty acids comprising at least two double bonds. PUFA may comprise three, four, five or six double bonds. PUFA may comprise, for example, from 18 to 24 carbon atoms in the fatty acid chain. Long chain PUFA ("LC-PUFA) can have, for example, from 20 to 24 carbon atoms in the fatty acid chain.

The term "omega-3 fatty acid" includes fatty acid, and may also include derivatives thereof such as triglycerides, esters and phospholipids. An omega-3 fatty acid has multiple double bonds each separated by methylene linkages. Counting from the terminal (w) carbon end of the fatty acid, a first double of an omega-3 fatty acid occurs between the third and fourth carbons from the terminal end. An omega-3 fatty acid may have, e.g., three double bonds, four double bonds, five double bonds or six double bonds. An omega-3 fatty acid may have all cis-double bonds. The term "long chain" omega-3 fatty acid as used herein refers to an omega-3 fatty acid having twenty (20) or more carbon atoms in the fatty acid chain.

The term "EPA" refers to an omega-3 fatty acid, all-cis-5,8,11,14,17-eicosapentaenoic acid, also represented as 20:5 (n-3). EPA is a long chain polyunsaturated fatty acid.

The term "DHA" refers to an omega-3 fatty acid, all-cis-4,7,10,13,16,19-docosahexaenoic acid also represented as 22:6 (n-3). DHA is a long chain polyunsaturated fatty acid.

The term "DPA" refers to an omega-3 fatty acid, all-cis-7,10,13,16,19-docosapentaenoic acid, also represented as 22:5 (n-3). DPA is a long chain polyunsaturated fatty acid.

The term "seed oil" or "oil from an oilseed plant" and related terms as used herein refer to an oil derived from seeds or other parts of an oilseed crop plant. In various aspects, the oil also may be chemically treated or refined in various ways, for example by degumming, refining, bleaching, dewaxing, and/or deodorizing. The seed oil may be oil from *Brassica* oilseed plants. The seed oil may be oil from transgenic *Brassica* oilseed plants. The oil from an oilseed plant may be canola oil. In various aspects, the oil includes one or more omega-3 fatty acids, such as, for example, EPA, DHA, DPA, ALA and SDA. The oil may include omega-3 fatty acids of eicosapentaenoic acid, docosahexaenoic acid and octadecatrienoic acid. Seed produced by methods of the present disclosure may be used to produce a commodity product such as, but not limited to, seed oil. The term "commodity product" refers to any product that is sold to consumers. Seed produced by the methods described herein may thus be used for food, feed, fuel or other commercial or industrial purposes or for purposes of growing or reproducing the species.

The term "transgenic oilseed plant" as used herein can refer to a plant species which has been genetically modified to produce long-chain omega-3 fatty acids such as EPA, DPA, and/or DHA. The resulting oil can be referred to as an "oil from a transgenically modified oilseed plant" or by similar terms. The terms transgenic, transgenically modified, modified or genetically modified are used here to distinguish the long-chain omega-3 fatty acid producing plants, or the oils derived from such plants, from those of other plant lines that do not produce long-chain omega-3 fatty acids. Without being limited to theory, the plants may have been modified to express the enzymes needed for production of EPA, DPA, and DHA from precursor fatty acids. If the oilseed plant is, for example, a *Brassica* or Camelina species, then the terms "transgenic *Brassica* oilseed plants" or "transgenic Camelina oilseed plant" may be used. The "transgenic oilseed plant" may also be transgenically modified in additional ways, such as for herbicide resistance or to modify the proportions of certain other fatty acids in its oil, in addition to having been modified to produce long-chain omega-3 fatty acids such as EPA, DPA, and/or DHA. In various aspects, the transgenic oilseed plant is compared to oilseed plant which has not been modified to produce long-chain omega-3 fatty acids such as EPA, DPA, and/or DHA. Such unmodified plant may yet still be a transgenic plant which has been modified in other ways, e.g., such as for herbicide resistance, but the plant is not modified such that it produces long-chain omega-3 fatty acids. Various aspects include the events discussed below.

As used herein, an "instructional material" includes a publication, a recording, a diagram, or any other medium of expression that can be used to communicate the usefulness of the invention in a kit for growth of *Brassica* plants as described herein. The instructional material of the kit of the invention may, for example, be affixed to a container that contains said *Brassica* seed for farming or be shipped together with a container that contains said *Brassica* seed. Alternatively, the instructional material may be shipped separately from said *Brassica* seed with the intention that the recipient use the instructional material and said *Brassica* seed cooperatively.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Definitions of particular terms may be contained within this section or may be incorporated into the sections of text below.

A "plurality" refers to any group having two or more members. A plurality of plants thus can be a group of 2 or more plants, a group of 10 or more plants, a group of 100 or more plants, a group of 1,000 or more plants, a group of 10,000 or more plants, a group of 100,000 or more plants, or a group of 1,000,000 or more plants. A plurality of plants can also be from 2 to 10 plants, from 2 to 100 plants, from 10 to 100 plants, from 100 to 1,000 plants, from 1,000 to 10,000 plants, from 10,000 to 100,000 plants, from 100,000 to 1,000,000 plants, from 1,000,000 to 10,000,000 plants.

The term "day" and "daily" as used herein refers to a 24-hour period. In various aspects, the 24-hour period is a calendar day.

The terms "comprises," "comprising," and the like can have the meaning ascribed to them in U.S. Patent Law and can mean "includes," "including" and the like. As used herein, "including" or "includes" or the like means including, without limitation.

Plants

As used herein, the term "*Brassica*" means any *Brassica* plant and includes all plant varieties that can be bred with *Brassica*. As defined herein, *Brassica* species include *B. napus, B. rapa, B. juncea, B. oleracea, B. nigra*, and *B. carinata*. In various aspects, the *Brassica* species comprises the LBFLFK and/or LBFDAU events. In various aspects, the *Brassica* species is *B. napus* comprising the LBFLFK and/or LBFDAU events, and progeny thereof. In various aspects, the *Brassica* plant may be a canola plant. The *Brassica* plant may be a hybrid.

The genus *Brassica* is known for its agricultural and horticultural crops. *Brassica* species and varieties commonly used for food include broccoli, cauliflower, cabbage, choy sum, rutabaga, turnip, and seeds used in the production of canola oil and the condiment mustard. Over 30 wild species and hybrids are in cultivation, plus numerous cultivars and hybrids of cultivated origin. Most are seasonal plants (annuals or biennials), but some are small shrubs. *Brassica* plants have been the subject of much scientific interest, especially in the area of agricultural, including species such as *B. carinata, B. juncea, B. oleracea, B. napus* (rapeseed, canola, rutabaga), *B. nigra*, and *B. rapa*.

In some aspects, the *Brassica* plant provided herein is a "canola" or low erucic acid, low glucosinolate rapeseed plant. Canola and/or low erucic rapeseed as used herein generally refers to plants of *Brassica* species that have less than 2% (e.g., less than 1%, 0.5%, 0.2% or 0.1%) erucic acid (delta 13-22:1) by weight in seed oil and/or less than 30 micromoles (e.g., less than 30, 25, 20 15, or 10 micromoles) of glucosinolates per gram of oil free meal (meal fraction). Typically, canola and/or rapeseed oil may include saturated fatty acids known as palmitic acid and stearic acid, a monounsaturated fatty acid known as oleic acid, and polyunsaturated fatty acids known as linoleic acid and linolenic acid. Canola oil and/or rapeseed oil may contain less than 7% (w/w) total saturated fatty acids (mostly palmitic acid and stearic acid) and greater than 40% (w/w) oleic acid (as percentages of total fatty acids). Traditionally, canola crops include varieties of *Brassica napus* and *Brassica rapa*. Non-limiting exemplary *Brassica* plants of the present disclosure are spring canola (*Brassica napus* subsp. oleifera var. *annua*) and winter canola (*Brassica napus* subsp. oleifera var. *biennis*). Furthermore, a canola quality *Brassica juncea* variety, which has oil and meal qualities similar to other canola types, has been added to the canola crop family (U.S. Pat. Nos. 6,303,849; 7,423,198). Likewise, it is possible to establish canola quality *B. carinata* varieties by crossing canola quality variants of *Brassica napus* with *Brassica nigra* and appropriately selecting progeny thereof, optionally after further back-crossing with *B. carinata, B. napus*, and/or *B. nigra*.

The term "canola" may refer to both canola plants and canola oil derived therefrom, depending on context. Canola as used herein is refers to the term's generic usage as a term for edible rapeseed oil and the plants from which they are derived, and also may refer to any codified usage of the term canola. For example, in various aspects, canola may meet the following requirements: seeds of the genus *Brassica* (*Brassica napus, Brassica rapa* or *Brassica juncea*) from which the oil shall contain less than 2% erucic acid in its fatty acid profile and the solid component shall contain less than 30 micromoles of any one or any mixture of 3-butenyl glucosinolate, 4-pentenyl glucosinolate, 2-hydroxy-3 butenyl glucosinolate, and 2-hydroxy-4-pentenyl glucosinolate per gram of air-dry, oil-free solid (Canola Council of Canada). In various aspects, canola may be any edible rapeseed oil or any plant from which edible rapeseed oil is derived. In various aspects, canola may be an edible rapeseed oil, or a plant which produces such oil. In various aspects, canola may be an edible rapeseed oil and also shall contain less than 2% erucic acid in its fatty acid profile, or a plant which produces such oil. In various aspects, canola may be an edible rapeseed oil and containing a solid component having less than 30 micromoles of any one or any mixture of 3-butenyl glucosinolate, 4-pentenyl glucosinolate, 2-hydroxy-3 butenyl glucosinolate, and 2-hydroxy-4-pentenyl glucosinolate per gram of air-dry, oil-free solid, or a plant which produces such oil. The term canola includes transgenic and non-transgenic canola.

As used herein, reference to an oilseed plant or plants includes the plant and its progeny, such as its Fi, F2, F3, F4, and subsequent generation plants. The plant or its progeny may be a hybrid. As used herein, a "line" or "breeding line" is a group of plants that display little or no genetic variation between individuals for at least one trait, such as a particular gene mutation or set of gene mutations. Such lines may be created by several generations of self-pollination and selection or by vegetative propagation from a single parent using tissue or cell culture techniques. A "variety" refers to a line that is used for commercial production and includes hybrid and open-pollinated varieties. As examples, the plant may include any of *Brassica*, flax, linseed, hemp, walnut, evening primrose, soy, sunflower, cotton, corn, olive, safflower, cocoa, peanut, hemp, Camelina, *crambe*, palm, coconut, sesame, castor bean, *lesquerella*, tallow, seanuts, tungnuts, kapok fruit, poppy, jojoba, *perilla*, or groundnut species. In various aspects, the oilseed plant is a *Brassica* species or Camelina species. *Brassica* plants may include, for example, *B. napus, B. juncea*, and *B. rapa* (rapeseed) species, while Camelina species include, for example, *C. sativa*. The oilseed plant or oilseed crop plant may be canola. The phrase "hybrid plants" refers to plants which result from a cross between genetically different individuals. The term "crossed" or "cross" in the context of this invention means the fusion of gametes, e.g., via pollination to produce progeny (i.e., cells, seeds, or plants) in the case of plants. The term encompasses both sexual crosses (the pollination of one plant by another) and, in the case of plants, selfing (self-pollination, i.e., when the pollen and ovule are from the same plant).

In various aspects, the growth stages of *Brassica* and other plants can, but are not required to, be understood according to the BBCH-scale, which lists growth stages including substages, from germination to harvest. For example, growth stages of canola plants may be understood according to the following growth stages from the BBCH-scale for canola:

Growth Stage 0—Germination
00. dry seed (seed dressing takes place at this stage)
01. seed imbibition (water absorption)
03. seed imbibition complete
05. radicle (root) emerges from seed
06. elongation of root, formation of root hairs and/or lateral roots
07. hypocotyl with cotyledons break though seed coat
08. hypocotyl with cotyledons grow toward soil surface
09. cotyledons break through soil surface
Growth Stage 1: Leaf Development
10. cotyledons completely unfold
11. first true leaf unfolds
12. two leaves unfold
13. three leaves unfold
14. four leaves unfold
15. five leaves unfold
16. six leaves unfold
17. seven leaves unfold
18. eight leaves unfold
19. nine or more leaves unfold
Growth Stage 2: Formation of side shoots
20. No side shoots
21. Beginning of side shoot development
29. End of side shoot development
Growth Stage 3: Stem Elongation
30. stem elongation (bolting) begins; or no internodes ("rosette")
31. stem 10% of final length or 1 visibly extended intemode
32. stem 20% of final length or 2 visibly extended intemode
33. stem 30% of final length or 2 visibly extended intemode
34. stem 40% of final length or 2 visibly extended intemode
35. stem 50% of final length or 2 visibly extended intemode
36. stem 60% of final length or 2 visibly extended intemode
37. stem 70% of final length or 2 visibly extended intemode
38. stem 80% of final length or 2 visibly extended intemode
39. maximum stem length or 9 visibly extended intemode
Growth Stage 4: (This BBCH stage omitted as it relates to booting)
Growth Stage 5: Inflorescence Emergence
50. flower buds present, but still enclosed by leave
51. flower buds visible from above (green bud)
52. flower buds free, level with the youngest leaves
53. flower buds raised above the youngest leaves
55. individual flower buds (main inflorescence) visible but still closed 58. individual flower buds (secondary inflorescence) visible but closed
59. first petals visible, but flower buds still closed (yellow bud)
Growth Stage 6: Flowering
60. first flowers open
61. 10% of flowers on the main raceme open, main raceme elongating
62. 20% of flowers on the main raceme open
63. 30% of flowers open on the main raceme
64. 40% of flowers on the main raceme open
65. full flowering—50% of flowers on main raceme open, older petals falling 67. flowering declining—majority of petals fallen
69. flowering ends
Growth Stage 7: Development of Seed
70. 0% of pods reach final size
71. 10% of pods reach final size
72. 20% of pods reach final size
73. 30% of pods reach final size
74. 40% of pods reach final size
75. 50% of pods reach final size
76. 60% of pods reach final size
77. 70% of pods reach final size
78. 80% of pods reach final size
79—nearly all of the pods reach final size
Growth Stage 8: Ripening
80. ripening begins—seed green, filling pod cavity
81. 10% of pods ripe, seeds black and hard
83. 30% of pods ripe, seeds black and hard
85. 50% of pods ripe, seeds black and hard
87. 70% of pods ripe, seeds black and hard
89. fully ripe—nearly all pods ripe, seeds black and hard
Growth Stage 9: Senescence
97. plants dead and dry
99. harvested product The term "first flower" refers to time at which the first 10% of plants in a plurality of plants have flowered. In instances where 10% of plants cannot be determined, e.g., due to the plurality of plants having fewer than 10 plants, "first flower" can be understood as the first point in time when at least 10% of plants have flowered. For example, if the plurality of plants is 5 plants, first flower would be when a single plant has flowered. In various aspects, "first flower" may correspond to BBCH-scale stage 6, substage 61.

The term "a period of seed maturation" as used herein can refer to a period from which the oilseeds first appear, through the period in which oilseeds grow and mature, and to the period when the plant is harvested. The period of seed maturation can also refer to a portion of such period. For example, in various aspects, the period of seed maturation may correspond to BBCH-scale stage 7, BBCH-scale stage 8, BBCH-scale stages 7 and 8 taken together, or BBCH-scale stages 6, 7 and 8 taken together. As further examples, the period of seed maturation may be from first appearance of full sized pods to harvest, or it may be from first appearance of ripe pods to harvest, or it may be from first appearance of green seeds in pods until harvest. The period of seed maturation may start at BBCH-scale substage 50, 51, 52, 53, 54, 55, 56, 57, 58, 59, 60, 61, 62, 63, 64, 65, 66, 67, 68, 69, 70, 71, 72, 73, 74, 75, 75, 76, 77, 78, 79, 80, 81, 82, 83, 84, 85, 86, 87, 88, or 89, and the period of seed maturation may end at BBCH-scale substage 60, 61, 62, 63, 64, 65, 66, 67, 68, 69, 70, 71, 72, 73, 74, 75, 75, 76, 77, 78, 79, 80, 81, 82, 83, 84, 85, 86, 87, 88, 89, 90, 91, 92, 93, 94, 95, 96, 97, 98 or 99.

Further structure and growth of a field crop, such as *Brassica*, is provided herein. The radicle (embryonic root) will emerge from the seed. Then, seedlings emerge, and two cotyledons (seed leaves) appear and the hypocotyl (embryonic stem) begins to extend upward. Chlorophyll and purple anthocyanin pigments can be apparent at this time. True leaves then develop, followed by the appearance of flower buds and elongation of the main stem or inflorescence (raceme). The stem elongates between the nodes (points of leaf attachment). The leaves and flower buds continue to enlarge, and secondary branches consisting of one to four leaves and a flower bud cluster emerge from the main raceme. As the stem elongates, the flower buds are raised to a height above the leaves. Then, flower buds open and reveal the flower structure. The pedicel, receptacle, sepals, petals, stamens (anthers and filaments), pistil (stigma, style, and ovary), and the nectaries can be identified. Pollination can be initiated at this time. After a period of time, petals change color and/or drop from the flowers, and pods elongate and swell. Endosperm and embryo development in the seeds has begun. The stages in embryo development can be observed by removing pods from the plant at different times, opening the pod to expose the ovules, and opening the ovules to expose the embryo. The embryo is surrounded by endosperm, a fine granular liquid that provides nutrients. Seeds are formed with seed coats from the integuments. The ovary walls and related structures have developed into the large pod (silique), and the pod begins to dry. As the seeds ripen, the pods turn yellow and/or brown, the embryo dehydrates, and the seed coat turns brown. Seeds can be harvested.

A raceme is an indeterminate type of inflorescence bearing pedicellate flowers (flowers having short floral stalks called pedicels) along its axis. In botany, an axis means a shoot, in this case one bearing the flowers. In indeterminate inflorescence-like racemes, the oldest flowers are borne towards the base and new flowers are produced as the shoot grows, with no predetermined growth limit (so the first/main raceme is the inflorescence that emerges first and the second branch/raceme is the one immediately below the first and so on and the oldest flower on the raceme is closest to the base). Examples of racemes occur on *Brassica* plants.

In some aspects, the *Brassica* plant can be any *Brassica* plant producing omega 3 fatty acids, including omega-3 docosahexaenoic acid (DHA), docosapentaenoic acid (DPA), and/or eicosapentaenoic acid (EPA).

In various aspects, the oilseed plants comprise event LBFLFK. Seed and progeny of event LBFLFK are also encompassed in this aspect. In another aspect, the oilseed plants comprise event LBFDAU. Seed and progeny of event LBFDAU are also encompassed in this aspect. Such oilseed plants may be *Brassica* plants. In particular, seeds with a LBFLFK or an LBFDAU event have been deposited at ATCC under the provisions of the Budapest treaty on the International Recognition of the Deposit of Microorganisms for the Purposes of Patent Procedure, i.e. seeds of event "LBFLFK"=ATCC Designation "PTA-121703" and seeds of event "LBFDAU"=ATCC Designation "PTA-122340 (LBFLFK and LBFDAU as described in PCT/EP2015/076632 (published as WO/2016/075327) and US 20180298400), which applications, publications, patents are incorporated by reference herein.

Some aspects comprise a *Brassica* plant containing one or more genes of the LBFLFK event. PCT/EP2015/076632 (published as WO/2016/075327) and US 20180298400 include molecular details of the construct used to generate the omega-3 LC-PUFA trait, and also the fatty acid composition of the seed oil. The genetic background for transgenesis was the variety 'Kumily', which is has low to no erucic acid but has oleic acid in the seed oil. The transgene cassette contains a Δ12-desaturase, Δ6-desaturase, Δ6-elongase, Δ5-desaturase, Δ5-elongase, Δ4-desaturase and ω3-desaturase. Each gene encoding an activity is under the regulation of a seed-specific promoter. In event LBFLFK, several activities are represented more than once—two copies of the Δ6-elongase and the Δ5-desaturase, and three copies of the ω3-desaturase. In these cases, genes from different organisms are used—for example, (synthetic) genes encoding the Δ6-elongase activity from both *Physcomitrella patens* and *Thalassiosira pseudonana* were used. Therefore, the transgene cassette contains 12 seed-specifically expressed omega-3 LC-PUFA biosynthetic genes (plus the AHAS gene which provides resistance against imadazolinone herbicides), representing a large transgene insert of ~44 Kb. Whole genome resequencing of the LBFLFK event revealed that this cassette was present twice in this transgenic canola line, being present intact on chromosomes C03 and Cnn. Thus, in total, 24 transgenes for the biosynthesis of EPA and DHA are present in event LBFLFK.

In various aspects, the transgenic oilseed plants of the invention comprise event LBFLFK (ATCC designation PTA-121703). Seed and progeny of event LBFLFK are also encompassed in this aspect. In another aspects, the transgenic oilseed plants of the invention comprise event LBFDAU (ATCC designation PTA-122340). Seed and progeny of event LBFDAU are also encompassed in this aspect. Such transgenic oilseed plants may be *Brassica* plants. Seeds of *Brassica* event LBFLFK (ATCC designation PTA-121703) and *Brassica* event LBFDAU (ATCC designation PTA-122340) have been deposited by applicant(s) at the American Type Culture Collection, Manassas, VA, USA, under the provisions of the Budapest Treaty on the International Recognition of the Deposit of Microorganisms for the Purposes of Patent Procedure. Applicants have no authority to waive any restrictions imposed by law on the transfer of biological material or its transportation in commerce. Applicants do not waive any infringement of their rights granted under this patent or rights applicable to the deposited events under the Plant Variety Protection Act (7 USC sec. 2321, et seq.), Unauthorized seed multiplication prohibited. This seed may be regulated according to national law. The deposition of seeds was made only for convenience of the person skilled in the art and does not constitute or imply any confession, admission, declaration or assertion that deposited seed are required to fully describe the invention, to fully enable the invention or for carrying out the invention or any part or aspect thereof.

The present disclosure may thus relate to plants LBFLFK and/or LBFDAU used to manufacture commodities typically acquired from *Brassica*. Seeds of LBFLFK and LBFDAU can be processed into meal or oil as well as be used as an oil source in animal feeds for both terrestrial and aquatic animals. The LC-PUFA-containing oil from events LBFLFK and/or LBFDAU may be used, for example, as a food additive to increase co-3 fatty acid intake in humans and animals, or in pharmaceutical compositions to enhance therapeutic effects thereof, or as a component of cosmetic compositions, and the like.

The LC-PUFA produced by the LBFLFK and LBFDAU events and their progeny can include DHGLA, ARA, ETA, EPA, DPA and DHA. The VLC-PUFA produced by the LBFLFK and LBFDAU events and their progeny can include ARA, EPA, and DHA. The VLC-PUFA produced by the LBFLFK and LBFDAU events and their progeny can include EPA and/or DHA. The LBFLFK and LBFDAU events and their progeny can also produce intermediates of LC-PUFA which occur during synthesis. Such intermediates may be formed from substrates by the desaturase, keto-acyl-CoA-synthase, keto-acyl-CoA-reductase, dehydratase and enoyl-CoA-reductase activity of the polypeptides of the present invention. Such substrates may include LA, GLA, DHGLA, ARA, eicosadienoic acid, ETA, and EPA.

LBFLFK and LBFDAU plants can be bred by first sexually crossing a first parental *Brassica* plant grown from the transgenic LBFLFK or LBFDAU *Brassica* plant (or progeny thereof) and a second parental *Brassica* plant that lacks the EPA/DHA profile and imidazolinone tolerance of the LBFLFK or LBFDAU event, respectively, thereby producing a plurality of first progeny plants and then selecting a first progeny plant that displays the desired imidazolinone tolerance and selfing the first progeny plant, thereby producing a plurality of second progeny plants and then selecting from the second progeny plants which display the desired imidazolinone tolerance and EPA/DHA profile. These steps can further include the back-crossing of the first EPA/DHA producing progeny plant or the second EPA/DHA producing progeny plant to the second parental *Brassica* plant or a third parental *Brassica* plant, thereby producing a *Brassica* plant that displays the desired imidazolinone tolerance and EPA/DHA profile. It is further recognized that assaying progeny for phenotype is not required. Various methods and compositions, as disclosed elsewhere, can be used to detect and/or identify the LBFLFK or LBFDAU event. (See, e.g., WO 2016/075303).

Two different transgenic plants can also be sexually crossed to produce offspring that contain two independently-segregating exogenous genes. Selfing of appropriate progeny can produce plants that are homozygous for both exogenous transgenic inserts. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in Breeding Methods for Cultivar Development, Wilcos, ed., American Society of Agronomy, Madison Wis. (1987), and Buzza, Plant Breeding, in *Brassica* Oilseeds: Production and Utilization. D. S. Kimber and D. I. McGregor eds. Cab International, Wallingford, UK (1995).

In various aspects, the transgenic oilseed plants may encompass plants described in or prepared using methods described in WO 2016/075327, which describes EPA and DHA producing *Brassica* lines and how to produce such lines, among other aspects. In various aspects, the modified oilseed crop plants may encompass plants described in or prepared using methods described in WO 2016/075325, which describes modification of plant lipids containing PUFAs, among other aspects. In various aspects, the modified oilseed crop plants may encompass plants described in or prepared using methods described in WO 2016/075303, which describes *Brassica* events and progeny thereof. In various aspects, the modified oilseed crop plants may encompass plants described in or prepared using methods described in WO 2015/089587, which describes EPA and DHA producing oilseed plants and how to produce such lines, among other aspects. In various aspects, the modified oilseed crop plants may encompass plants described in or prepared using methods described in WO 2004/071467, which describes EPA and DHA producing *Brassica* lines and how to produce such lines, among other aspects. In various aspects, the modified oilseed crop plants may encompass plants described in or prepared using methods described in U.S. Pat. No. 7,807,849 B2, which describes EPA and DHA producing *Arabidopsis* lines and how to produce such lines. In various aspects, the modified oilseed crop plants may encompass plants described in or prepared using methods described in WO 2013/153404, which describes EPA and DHA producing Camelina lines and how to produce such lines. Each of these documents are incorporated by reference herein in their entirety for their disclosures of modified plant lines and how to produce such lines.

In other aspects, the oilseed plants comprise event NS-B50027-4. Seed and progeny of event NS-B50027-4 are also encompassed in this aspect. Such oilseed plants may be *Brassica* plants. In particular, seeds with a NS-B50027-4 event have been deposited at ATCC under the provisions of the Budapest treaty on the International Recognition of the Deposit of Microorganisms for the Purposes of Patent Procedure, i.e. seeds of event "NS-B50027-4"=ATCC Designation "PTA-123186" (NS-B50027-4 as described in PCT/US2017/038047 (published as WO/2017/219006), which applications, publications, patents are incorporated by reference herein.

The genetic background used for the transgenic canola event NS-B50027-4 is the variety 'AV Jade', which is also a low to zero-erucic acid type and produces oleic acid. The transgene cassette used to introduce the omega-3 LC-PUFA trait contains all the same gene types as LBFLFK event under the regulation of a seed-specific promoter. Unlike LBFLFK event, each biosynthetic activity is represented by a single gene, and herbicide tolerance to glufosinate is conferred by the phosphinothricin acetyltransferase gene, meaning the predicted overall size of the insertion is ~23 Kb. In event NS-B50027-4, the source organisms from which the biosynthetic activities were obtained are different from those described for the LBFLFK event.

A transgenic "event" can be produced, for example, by transformation of plant cells with a heterologous DNA construct(s) including a nucleic acid expression cassette that comprises one or more transgene(s) of interest, the regeneration of a population of plants from cells which each comprise the inserted transgene(s) and selection of a particular plant characterized by insertion into a particular genome location. An event can be characterized phenotypically by the expression of the transgene(s). At the genetic level, an event can be part of the genetic makeup of a plant. The term "event" refers to the original transformant and progeny of the transformant that include the heterologous DNA. The term "event" also refers to progeny, produced by a sexual outcross between the transformant and another variety, that include the heterologous DNA. Even after repeated back-crossing to a recurrent parent, the inserted DNA and flanking DNA from the transformed parent are present in the progeny of the cross at the same chromosomal location. The term "event" also refers to DNA from the original transformant comprising the inserted DNA and flanking sequence immediately adjacent to the inserted DNA that would be expected to be transferred to a progeny as the result of a sexual cross of one parental line that includes the inserted DNA (e.g., the original transformant and progeny resulting from selfing) and a parental line that does not contain the inserted DNA. As used herein, "insert DNA" can refer to the heterologous DNA within the expression cassettes used to transform the plant material while "flanking DNA" can comprise either genomic DNA naturally present in an organism such as a plant, or foreign (heterologous) DNA introduced via the transformation process which is extraneous to the original insert DNA molecule, e.g. fragments associated with the transformation event. A "flanking region" or "flanking sequence" as used herein refers to a sequence of at least 20, 50, 100, 200, 300, 400, 1000, 1500, 2000, 2500 or 5000 base pairs or greater which is located either immediately upstream of and contiguous with, or immediately downstream of and contiguous with, the original foreign insert DNA molecule. Progeny of the *Brassica* LBFLFK event may comprise either FBFFFK Focus 1 or FBFFFK Focus 2, or both FBFFFK Focus 1 and FBFFFK Focus 2; progeny of the *Brassica* FBFDAU event may comprise either FBFDAU Focus 1 or FBFDAU Focus 2, or both FBFDAU Focus 1 and FBFDAU Focus 2. For examples of these events and others, and how such events can be incorporated into an oilseed crop, see WO 2016/075303, WO 2016/075325 and WO 2016/075327, each of which is incorporated by reference in its entirety.

In some aspects, the disclosure provides a *Brassica* plant or a part thereof comprising one or more exogenous polynucleotides heritably integrated into its genome, the exogenous polynucleotides comprising one or more expression cassettes having nucleotide sequences encoding one or more Δ12-desaturase, Δ6-desaturase, Δ6-elongase, Δ5-desaturase, Δ5-elongase, Δ4-desaturase and/or ω3-desaturase.

The term "desaturase" encompasses all enzymatic activities and enzymes catalyzing the desaturation of fatty acids with different lengths and numbers of unsaturated carbon atom double bonds. For example, a desaturase can be a delta 4 (d4)-desaturase that catalyzes the dehydrogenation of the 4th and 5th carbon atom; a delta 5 (d5)-desaturase catalyzing the dehydrogenation of the 5th and 6th carbon atom; a delta 6 (d6)-desaturase catalyzing the dehydrogenation of the 6th and 7th carbon atom; a delta 8 (d8)-desaturase catalyzing the dehydrogenation of the 8th and 9th carbon atom; a delta 9 (d9)-desaturase catalyzing the dehydrogenation of the 9th and 10th carbon atom; a delta 12 (d12)-desaturase catalyzing the dehydrogenation of the 12th and 13th carbon atom; or a delta 15 (d15)-desaturase catalyzing the dehydrogenation of the 15th and 16th carbon atom.

The terms "elongase" encompasses all enzymatic activities and enzymes catalyzing the elongation of fatty acids with different lengths and numbers of unsaturated carbon atom double bonds. In some aspects, the term "elongase" refers to the activity of an elongase that introduces two carbon molecules into the carbon chain of a fatty acid.

Polynucleotides encoding polypeptides that exhibit delta-6-elongase activity have been described, for example, in WO2001/059128, WO2004/087902, WO2005/012316, and WO 2015/089587, which are incorporated herein in their entirety. Non-limiting exemplary delta-6-elongases include those from *Physcomitrella patens* and *Pyramimonas cordata*.

Polynucleotides encoding polypeptides which exhibit delta-5-desaturase (d5Des) activity have been described, for example, in WO2002/026946, WO2003/093482, and WO 2015/089587, which are incorporated herein in their entirety. Non-limiting exemplary delta-5-desaturases include those from *Thraustochytrium* sp., *Pavlova sauna*, and *Pyramimonas cordata*.

Polynucleotides encoding polypeptides which exhibit delta-6-desaturase activity have been described in WO2005/012316, WO2005/083093, WO2006/008099 and WO2006/ 069710, and WO 2015/089587, which are incorporated herein in their entirety. Non-limiting exemplary delta-6-desaturases include those from *Ostreococcus tauri*, *Micromonas pusilla*, and *Osreococcus lucimarinus*.

Polynucleotides encoding polypeptides which exhibit delta-5-elongase activity have been described in WO2005/012316, WO2005/007845, WO2007/096387, WO2006/

069710, and WO 2015/089587, which are incorporated herein in their entirety. Non-limiting exemplary delta-5-elongases include those from *Ostreococcus tauri* and *Pyramimonas cordata*.

Polynucleotides encoding polypeptides which exhibit delta-12-desaturase activity have been described for example in WO2006100241 and WO 2015/089587, which are incorporated herein in their entirety. Non-limiting exemplary delta-12-desaturases include those from *Phytophthora sojae* and *Lachancea kluyveri*.

Polynucleotides encoding polypeptides which exhibit delta-4-desaturase (d4Des) activity have been described for example in WO2004/090123, WO2002026946, WO2003078639, WO2005007845, and WO 2015/089587, which are incorporated herein in their entirety. Non-limiting exemplary delta-4-desaturases include those from *Euglena gracilis*, *Thraustochytrium* sp., *Pavlova lutheri*, and *Pavlova sauna*. See, e.g., delta-4 desaturase "P1DES 1" and FIGS. 3*a*-3*d* of WO2003078639 and FIGS. 3*a*, 3*b* of WO2005007845, respectively.

Polynucleotides encoding polypeptides which exhibit omega 3-desaturase (o3Des) activity have been described for example in WO2008/022963, WO2005012316, WO2005083053, and WO 2015/089587, which are incorporated herein in their entirety. Non-limiting exemplary omega-3-desaturases include those from *Phytium irregular*, *Phytophthora infestans*, and *Pichia pastoris*.

Polynucleotides encoding polypeptides which exhibit delta-15-desaturase activity have been described for example in WO2010/066703, which is incorporated herein in its entirety. Non-limiting exemplary delta-15 destaurases include the delta-15 desaturase from *Cochliobolus heterostrophus* C5.

Additional polynucleotides that encode polypeptides having desaturase or elongase activities as specified above can be obtained from various organisms, including but not limited to, organisms of genus *Ostreococcus*, *Thraustochytrium*, *Euglena*, *Thalassiosira*, *Phytophthora*, *Phytium*, *Cochliobolus*, or *Physcomitrella*. Orthologs, paralogs or other homologs having suitable desaturase or elongase activities may be identified from other species. In some aspects, such orthologs, paralogs, or homologs are obtained from plants such as algae, for example *Isochrysis*, *Mantoniella*, or *Crypthecodinium*, algae/diatoms such as *Phaeodactylum*, mosses such as *Ceratodon*, or higher plants such as the Primulaceae such as *Aleuritia*, *Calendula stellata*, *Osteospermum spinescens* or *Osteospermum hyoseroides*, microorganisms such as fungi, such as *Aspergillus*, *Entomophthora*, *Mucor* or *Mortierella*, bacteria such as *Shewanella*, yeasts or animals. Non-limiting exemplary animals are nematodes such as *Caenorhabditis*, insects or vertebrates. Among the vertebrates, the nucleic acid molecules may, in some aspects, be derived from *Euteleostomi*, *Actinopterygii*; *Neopterygii*; *Teleostei*; *Euteleostei*, *Protacanthopterygii*, Salmoniformes; Salmonidae or *Oncorhynchus*, such as from the order of the Salmoniformes, such as the family of the Salmonidae, such as the genus *Salmo*, for example from the genera and species *Oncorhynchus mykiss*, *Trutta trutta* or *Salmo trutta fario*. Moreover, the nucleic acid molecules may be obtained from the diatoms such as the genera *Thalassiosira* or *Phaeodactylum*.

For example, some aspects provide a *Brassica* plant or a part thereof comprising one or more exogenous polynucleotides heritably integrated into its genome, the exogenous polynucleotides comprising one or more expression cassettes having nucleotide sequences encoding one or more d12DES, one or more d6Elo, one or more d6Des, one or more d5Des, one or more d5Elo, one or more d4Des, and/or one or more o3Des. The plant can be the result of crossing a first parental *Brassica* plant that comprises the one or more exogenous polynucleotides with a second parental *Brassica* plant. The *Brassica* plant can produce in its seeds a greater amount of one or more polyunsaturated fatty acids selected from the group consisting of EPA, DPA, and DHA than the first parental *Brassica* plant and/or the second parental *Brassica* plant. A part of a *Brassica* plant includes any parts derived from a plant, including cells, tissues, roots, stems, leaves, non-living harvest material, silage, seeds, seed meals and pollen.

Seed Oil Composition

The fertilizer methods provided herein provide increased production of long chain omega 3 fatty acids, including omega-3 docosahexaenoic acid (DHA), docosapentaenoic acid (DPA), and/or eicosapentaenoic acid (EPA), at elevated levels in seeds of *Brassica* plant seeds. In some aspects, seeds of *Brassica* plants provided herein can produce higher levels of EPA, higher levels of DPA, higher levels of DHA, higher levels of EPA and DHA, higher levels of DHA and DPA, higher levels of DPA and EPA, or higher levels of EPA, DHA, and DPA, as compared to plants not grown according to the methods described herein. In some aspects, EPA is increased more than DPA and DHA. In some aspects, EPA is increased 0.2% to 0.6%%, including 0.3% to 0.5% (with a percent increases of 3-6%), DPA is increased 0.1% to 0.3, including 0.04% to 0.08% (what percent increase of 3-7), and/or DHA is increased 0.02% to 0.14%, including 0.03% (with a percent increase of 7-20%). In some aspects, the amount of increase in EPA+DPA+DHA is at least 1.2% to 1.8%, including 0.4% to 0.7% (with a percent increase of 3.9-7%).

Fertilizer Amount

A fertilizer is any material of natural or synthetic origin that is applied to soil or to plant tissues to supply one or more plant nutrients to the growth of plants, such as a nitrogenous fertilizer. Fertilizers typically contain nitrogen. Varying amounts of nitrogen can be applied to plants to aid in their growing cycle. For example, a standard level of applied nitrogen for *Brassica* crops is about 125 lbs/acre for a dryland (not irrigated by man) location, and 175 lbs/acre for an irrigated location. Nitrogen can be applied dry or wet (as a liquid).

When nitrogen amount is increased over the standard amount there is not necessarily a change, or there could even be a decrease, in total oil yield; however, a change in the proportion of the oil that is EPA, DPA and DHA occurs.

In one aspect, in order to obtain an increased amount of long chain omega 3 fatty acids, such as DHA, DPA and/or EPA, in *Brassica* seeds which comprise omega 3 fatty acids (for example, contain an event described above), the plants are grown under conditions in which nitrogen is applied at a 30-50% increase over a standard amount nitrogen applied to a field/field crop, including *Brassica*. In one aspect, the increase is 30%, 31%, 32%, 33%, 34%, 35%, 36%, 37%, 38%, 39%, 40%, 41%, 42%, 43%, 44%, 45%, 46%, 47%, 48%, 49% or 50% over a standard amount of nitrogen applied to a field for the growth of a crop, including *Brassica*.

In one aspect, in order to obtain an increased amount of long chain omega 3 fatty acids, such as DHA, DPA and/or EPA, in *Brassica* seeds which comprise omega 3 fatty acids (for example, contain an event described above), the plants are grown under conditions in which in addition to a standard amount of nitrogen, an additional 30 lbs/acre to 90 lbs/acre, including 30 lbs/acre to 70 lbs/acre and 70 lbs/acre to 90 lbs/acre, including 50 lbs/acre and 70 lbs/acre, of nitrogen applied to a field/field crop, including *Brassica*. In one aspect, an additional 30 lbs/acre, 3 lbs/acre, 32 lbs/acre, 33 lbs/acre, 34 lbs/acre, 35 lbs/acre, 35 lbs/acre, 36 lbs/acre, 37 lbs/acre, 38 lbs/acre, 39 lbs/acre, 40 lbs/acre, 4 lbs/acre, 42 lbs/acre, 43 lbs/acre, 44 lbs/acre, 45 lbs/acre, 46 lbs/acre, 47 lbs/acre, 48 lbs/acre, 49 lbs/acre, 50 lbs/acre, 51 lbs/acre, 52 lbs/acre, 53 lbs/acre, 54 lbs/acre, 55 lbs/acre, 56 lbs/acre, 57 lbs/acre, 58 lbs/acre, 59 lbs/acre, 60 lbs/acre, 61 lbs/acre, 62 lbs/acre, 63 lbs/acre, 64 lbs/acre, 65 lbs/acre, 66 lbs/acre, 67 lbs/acre, 68 lbs/acre, 69 lbs/acre, 70 lbs/acre, 71 lbs/acre, 72 lbs/acre, 73 lbs/acre, 74 lbs/acre, 75 lbs/acre, 76 lbs/acre, 77 lbs/acre, 78 lbs/acre, 79 lbs/acre, 80 lbs/acre, 81 lbs/acre, 82 lbs/acre, 83 lbs/acre, 84 lbs/acre, 85 lbs/acre, 86 lbs/acre, 87 lbs/acre, 88 lbs/acre, 89 lbs/acre or 90 lbs/acre nitrogen over a standard amount of nitrogen applied to a filed for the growth of a crop, included *Brassica*. In one aspect, the standard amount nitrogen is 100 lbs/acre to 200 lbs/acre, including 100 lbs/acre to 150 lbs/acre, including 125 lbs/acre and including 150 lbs/acre to 200 lbs/acre including 175 lbs/acre, such as 100 lbs/acre, 101 lbs/acre, 102 lbs/acre, 103 lbs/acre, 104 lbs/acre, 105 lbs/acre, 106 lbs/acre, 107 lbs/acre, 108 lbs/acre, 109 lbs/acre, 110 lbs/acre, 111 lbs/acre, 112 lbs/acre, 113 lbs/acre, 114 lbs/acre, 115 lbs/acre, 11 lbs/acre, 117 lbs/acre, 118 lbs/acre, 119 lbs/acre, 120 lbs/acre, 121 lbs/acre, 122 lbs/acre, 12 lbs/acre, 124 lbs/acre, 125 lbs/acre, 126 lbs/acre, 127 lbs/acre, 128 lbs/acre, 129 lbs/acre, 130 lbs/acre, 131 lbs/acre, 132 lbs/acre, 133 lbs/acre, 134 lbs/acre, 135 lbs/acre, 136 lbs/acre, 137 lbs/acre, 138 lbs/acre, 139 lbs/acre, 140 lbs/acre, 141 lbs/acre, 142 lbs/acre, 143 lbs/acre, 144 lbs/acre, 145 lbs/acre, 146 lbs/acre, 147 lbs/acre, 148 lbs/acre, 149 lbs/acre, 150 lbs/acre, 151 lbs/acre, 152 lbs/acre, 153 lbs/acre, 154 lbs/acre, 155 lbs/acre, 156 lbs/acre, 157 lbs/acre, 158 lbs/acre, 159 lbs/acre, 160 lbs/acre, 161 lbs/acre, 162 lbs/acre, 163 lbs/acre, 164 lbs/acre, 165 lbs/acre, 166 lbs/acre, 167 lbs/acre, 168 lbs/acre, 169 lbs/acre, 170 lbs/acre, 171 lbs/acre, 172 lbs/acre, 173 lbs/acre, 174 lbs/acre, 175 lbs/acre, 176 lbs/acre, 177 lbs/acre, 178 lbs/acre, 179 lbs/acre, 180 lbs/acre, 181 lbs/acre, 182 lbs/acre, 183 lbs/acre, 184 lbs/acre, 185 lbs/acre, 186 lbs/acre, 187 lbs/acre, 188 lbs/acre, 189 lbs/acre, 190 lbs/acre, 191 lbs/acre, 192 lbs/acre, 193 lbs/acre, 194 lbs/acre, 195 lbs/acre, 196 lbs/acre, 197 lbs/acre, 198 lbs/acre, 199 lbs/acre or 200 lbs/acre or more.

Harvest Time

In one aspect, in order to obtain increased amount of long chain omega 3 fatty acids, such as DHA, DPA and/or EPA, in *Brassica* seeds which comprise omega 3 fatty acids (e.g., contain an event described above), the plants are harvested, such as swathed or straight cut, when 80% to 100% (including 80% and/or 100%, e.g., 80% and/or 100%) color change has occurred on the main raceme (meaning the main raceme (also known as first raceme) is 80% to 100% yellow and/or brown) averaging throughout the crop (meaning that the majority of plants to be harvested in the plot being harvested will have 80% to 100% color change on the main raceme). In another aspect, in order to obtain increased amount of DHA, DPA and/or EPA in *Brassica* seeds which comprise omega 3 fatty acids, the plants are harvested when 80% to 100% (including 80% and/or 100% color change has occurred on the main, second, third and/or fourth raceme or a combination thereof (meaning the main, second, third and/or fourth raceme is/are 80% to 100% yellow and/or brown) averaging throughout the crop.

The invention will be further described in the following example, which does not limit the scope of the invention described in the claims.

EXAMPLE

Example 1: Fertilizer Management

During a field season M11 was sown in late April-early May at 10-12 plants per square foot at 10 locations (3 dryland, 7 irrigated) in Montana. Soil testing for available nitrogen was conducted at all sites and two treatments were applied. Treatment 1 (standard): Starting available nitrogen level of 125 lbs/acre if dryland location, and 175 lbs/acre if irrigated location; Treatment 2: Starting nitrogen level as per treatment 1 PLUS an extra 50 lb/acre for dryland locations and 70 lb/acre for irrigated locations, applied as a liquid at sowing. Plots were managed as normal R&D plots through the season and harvested by straight cut after desiccation at physiological maturity (seeds have all matured and turned color, plant is dry and can be combined (but not excessively shattering everywhere)). A representative seed sample was analyzed for fatty acid profile. Nine plot replicates were analyzed for each treatment and each genotype. EPA, DPA and DHA were increased in all samples that received Treatment 2 (the extra nitrogen application). EPA levels in dryland plants rose significantly with a 0.462% increase and those in irrigated locations showed a 0.303% significant increase. DPA levels in dryland plants rose significantly with an increase of 0.1% and those in irrigated locations showed a significant increase of 0.0646%. DHA levels in dryland rose significantly with a 0.1266% increase and those in irrigated locations showed a significant increase of 0.0451%. The analysis was a standard ANOVA which looked at the mean performance of the expressions of the line with the different treatments applied. Statistical significance meant that at a 95% confidence interval we can see that there was a difference in all components of omega expression between the two treatments.

While there appeared to be no change in overall oil yield, there was a change/increase in EPA, DPA and DHA with irrigated land. In dry land (meaning not irrigated), there was actually a decrease in total oil yield, but an increase in EPA, DPA, and DHA. Thus, when nitrogen amount is increased over the standard amount there is not necessarily a change, or there could even be a decrease, in total oil yield; however, a change in the proportion of the oil that is EPA, DPA and DHA occurs.

TABLE 1

| DRYLAND EPA | | |
| --- | --- | --- |
| name | M11 | |
| Treatment 1 | 7.557 | a |
| Treatment 2 | 8.019 | b |
| LSD | 0.1422 | |
| DPA | | |
| name | M11 | |
| Treatment 1 | 1.581 | a |
| Treatment 2 | 1.681 | b |
| LSD | 0.0392 | |
| DHA | | |
| name | M11 | |
| Treatment 1 | 0.6533 | a |
| Treatment 2 | 0.7799 | b |
| LSD | 0.02288 | |
| IRRIGATED EPA | | |
| name | M11 | |
| Treatment 1 | 8.001 | a |

TABLE 1-continued

| | | |
| --- | --- | --- |
| Treatment 2 | 8.304 | b |
| LSD | 0.1615 | |
| DPA | | |
| name | M11 | |
| Treatment 1 | 1.8618 | a |
| Treatment 2 | 1.9264 | b |
| LSD | 0.04047 | |
| DHA | | |
| name | M11 | |
| Treatment 1 | 0.6179 | a |
| Treatment 2 | 0.663 | b |
| LSD | 0.01603 | |

All publications, patents, and patent applications mentioned in this specification are herein incorporated by reference to the same extent as if each individual publication, patent, or patent application was specifically and individually indicated to be incorporated by reference. In the event that the definition of a term incorporated by reference conflicts with a term defined herein, this specification shall control.

What is claimed is:

1. A method to increase a proportion of long-chain omega-3 fatty acid in seed oil produced by a plurality of *Brassica* oilseed plants comprising growing the *Brassica* oilseed plants in the presence of an increased amount of nitrogen as compared to a standard amount of nitrogen, wherein the *Brassica* oilseed plants have been modified to produce seed oil with at least one of eicosapentaenoic acid (EPA), docosahexaenoic acid (DHA), and docosapentaenoic acid (DPA), wherein the standard amount of nitrogen is 100 lbs/acre to 200 lbs/acre, and wherein the *Brassica* oilseed plants comprise exogenous polynucleotides encoding a Δ12-desaturase, a 46-desaturase, a Δ6-elongase, a 45-desaturase, a Δ5-elongase, a Δ4-desaturase, and a ω3-desaturase.

2. The method of claim 1, wherein the increased amount of nitrogen is 30-50% increase over a standard amount nitrogen.

3. The method of claim 1, wherein the increased amount of nitrogen is 30%, 31%, 32%, 33%, 34%, 35%, 36%, 37%, 38%, 39%, 40%, 41%, 42%, 43%, 44%, 45%, 46%, 47%, 48%, 49% or 50% increase over a standard amount nitrogen.

4. The method claim 1, wherein the increased amount of nitrogen is 30 lbs/acre to 90 lbs/acre, 30 lbs/acre to 70 lbs/acre, 70 lbs/acre to 90 lbs/acre, 50 lbs/acre or, 70 lbs/acre increase over a standard amount nitrogen.

5. The method of claim 1, wherein the increased amount nitrogen is 30 lbs/acre, 31 lbs/acre, 32 lbs/acre, 33 lbs/acre, 34 lbs/acre, 35 lbs/acre, 35 lbs/acre, 36 lbs/acre, 37 lbs/acre, 38 lbs/acre, 39 lbs/acre, 40 lbs/acre, 41 lbs/acre, 42 lbs/acre, 43 lbs/acre, 44 lbs/acre, 45 lbs/acre, 46 lbs/acre, 47 lbs/acre, 48 lbs/acre, 49 lbs/acre, 50 lbs/acre, 51 lbs/acre, 52 lbs/acre, 53 lbs/acre, 54 lbs/acre, 55 lbs/acre, 56 lbs/acre, 57 lbs/acre, 58 lbs/acre, 59 lbs/acre, 60 lbs/acre, 61 lbs/acre, 62 lbs/acre, 63 lbs/acre, 64 lbs/acre, 65 lbs/acre, 66 lbs/acre, 67 lbs/acre, 68 lbs/acre, 69 lbs/acre, 70 lbs/acre, 71 lbs/acre, 72 lbs/acre, 73 lbs/acre, 74 lbs/acre, 75 lbs/acre, 76 lbs/acre, 77 lbs/acre, 78 lbs/acre, 79 lbs/acre, 80 lbs/acre, 81 lbs/acre, 82 lbs/acre, 83 lbs/acre, 84 lbs/acre, 85 lbs/acre, 86 lbs/acre, 87 lbs/acre, 88 lbs/acre, 89 lbs/acre, or 90 lbs/acre nitrogen over a standard amount of nitrogen.

6. The method of claim 1, wherein the standard amount of nitrogen is 100 lbs/acre, 101 lbs/acre, 102 lbs/acre, 103 lbs/acre, 104 lbs/acre, 105 lbs/acre, 106 lbs/acre, 107 lbs/acre, 108 lbs/acre, 109 lbs/acre, 110 lbs/acre, 111 lbs/acre, 112 lbs/acre, 113 lbs/acre, 114 lbs/acre, 115 lbs/acre, 11 lbs/acre, 117 lbs/acre, 118 lbs/acre, 119 lbs/acre, 120 lbs/acre, 121 lbs/acre, 122 lbs/acre, 12 lbs/acre, 124 lbs/acre, 125 lbs/acre, 126 lbs/acre, 127 lbs/acre, 128 lbs/acre, 129 lbs/acre, 130 lbs/acre, 131 lbs/acre, 132 lbs/acre, 133 lbs/acre, 134 lbs/acre, 135 lbs/acre, 136 lbs/acre, 137 lbs/acre, 138 lbs/acre, 139 lbs/acre, 140 lbs/acre, 141 lbs/acre, 142 lbs/acre, 143 lbs/acre, 144 lbs/acre, 145 lbs/acre, 146 lbs/acre, 147 lbs/acre, 148 lbs/acre, 149 lbs/acre, 150 lbs/acre, 151 lbs/acre, 152 lbs/acre, 153 lbs/acre, 154 lbs/acre, 155 lbs/acre, 156 lbs/acre, 157 lbs/acre, 158 lbs/acre, 159 lbs/acre, 160 lbs/acre, 161 lbs/acre, 162 lbs/acre, 163 lbs/acre, 164 lbs/acre, 165 lbs/acre, 166 lbs/acre, 167 lbs/acre, 168 lbs/acre, 169 lbs/acre, 170 lbs/acre, 171 lbs/acre, 172 lbs/acre, 173 lbs/acre, 174 lbs/acre, 175 lbs/acre, 176 lbs/acre, 177 lbs/acre, 178 lbs/acre, 179 lbs/acre, 180 lbs/acre, 181 lbs/acre, 182 lbs/acre, 183 lbs/acre, 184 lbs/acre, 185 lbs/acre, 186 lbs/acre, 187 lbs/acre, 188 lbs/acre, 189 lbs/acre, 190 lbs/acre, 191 lbs/acre, 192 lbs/acre, 193 lbs/acre, 194 lbs/acre, 195 lbs/acre, 196 lbs/acre, 197 lbs/acre, 198 lbs/acre, 199 lbs/acre, or 200 lbs/acre.

7. The method of claim 1, wherein the nitrogen is applied dry, wet, or a combination thereof.

8. The method of claim 1, wherein the *Brassica* oilseed plants are planted in a field.

9. The method of claim 8, wherein the fields are irrigated.

10. The method of claim 8, wherein the fields are not irrigated.

11. The method of claim 1, wherein the *Brassica* oilseed plants are *Brassica napus* plants.

12. The method of claim 1, wherein the proportion of omega-3 fatty acid in the seed oil is increased in the presence of an increased amount of nitrogen during growth in comparison to control *Brassica* oilseed plants grown in the presence of a standard amount of nitrogen.

13. The method of claim 1, wherein a percent increase in combined EPA, DPA, and DHA when grown in the presence of an increased amount of nitrogen is 3.9-7%.

14. The method of claim 1, wherein a percent increase in EPA when grown in the presence of an increased amount of nitrogen is 3-6%.

15. The method of claim 1, wherein a percent increase in DPA when grown in the presence of an increased amount of nitrogen is 3-7%.

16. The method of claim 1, wherein a percent increase in DHA when grown in the presence of an increased amount of nitrogen is 7-20%.

17. The method of claim 1, wherein the *Brassica* plants are harvested when 80% to 100% color change has occurred on the first raceme of the plants.

18. The method of claim 17, wherein the color change has further occurred on 80% to 100% of the second, third, and/or fourth raceme of the plants.

19. The method of claim 18, wherein the color change has occurred on 80% to 100% of the third raceme of the plants.

20. The method of claim 1, wherein the *Brassica* oilseed plants comprise event LBFLFK and/or event LBFDAU.

21. The method of claim 20, wherein the *Brassica* oilseed plants comprise event LBFLFK.

22. The method of claim 21, wherein the *Brassica* oilseed plants are *Brassica napus* plants.

\* \* \* \* \*